United States Patent

Pharriss et al.

[11] 4,016,270
[45] Apr. 5, 1977

[54] METHOD FOR TREATING DYSMENORRHEA WITH A UTERINE THERAPEUTIC SYSTEM

[75] Inventors: Bruce B. Pharriss, Palo Alto; Ross R. Erickson, Sunnyvale; Stephen A. Tillson, Los Altos, all of Calif.

[73] Assignee: Alza Corporation, Palo Alto, Calif.

[22] Filed: Oct. 31, 1975

[21] Appl. No.: 627,591

[52] U.S. Cl. ............................................. 424/242
[51] Int. Cl.$^2$ ...................................... A61K 31/56
[58] Field of Search ............ 424/242, 243; 128/130

[56] References Cited
UNITED STATES PATENTS

| 3,800,038 | 3/1974 | Rudel | 424/242 |
| 3,892,842 | 7/1975 | Zaffaroni | 424/242 |
| 3,895,103 | 7/1975 | Zaffaroni | 424/242 |

OTHER PUBLICATIONS

Bishop, P.M. A New Oral Progestogen in the Treatment of Dysmenorrhoea, Proc. Roy. Soc. Med. 54: pp. 752–754.

Primary Examiner—Elbert L. Roberts
Attorney, Agent, or Firm—Paul L. Sabatine; Thomas E. Ciotti; Edward L. Mandell

[57] ABSTRACT

A method for treating dysmenorrhea is disclosed. The method comprises administering to the uterus of a warm blooded animal having dysmenorrhea controlled and continuous low dosage amounts of a progestational hormone to impart symptomatic relief from dysmenorrhea.

19 Claims, 8 Drawing Figures

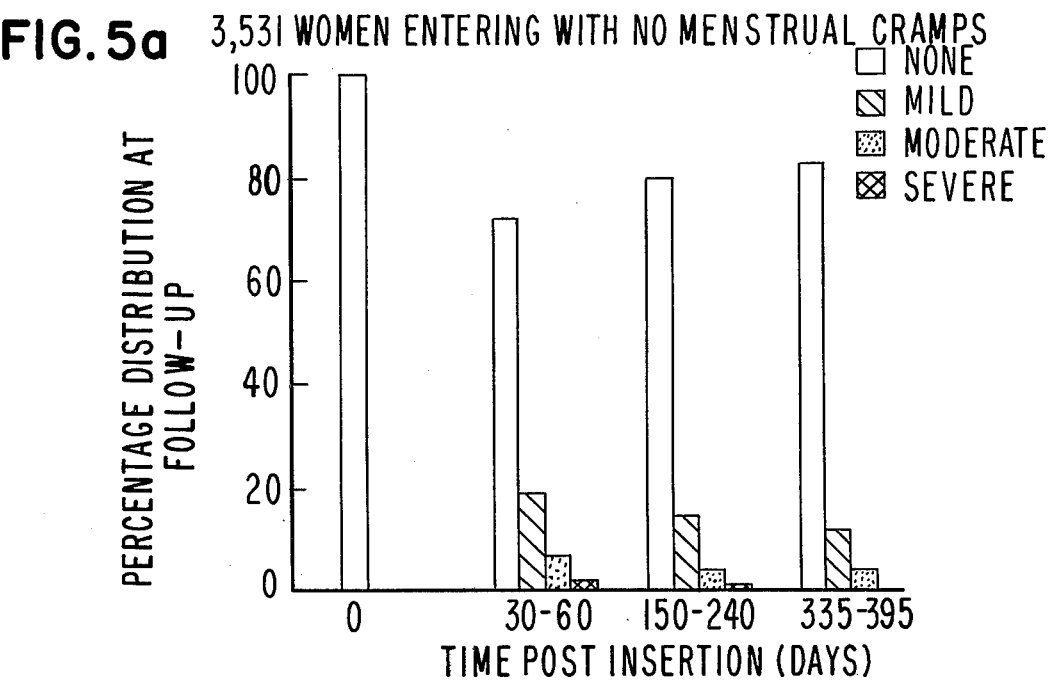
FIG. 5a 3,531 WOMEN ENTERING WITH NO MENSTRUAL CRAMPS
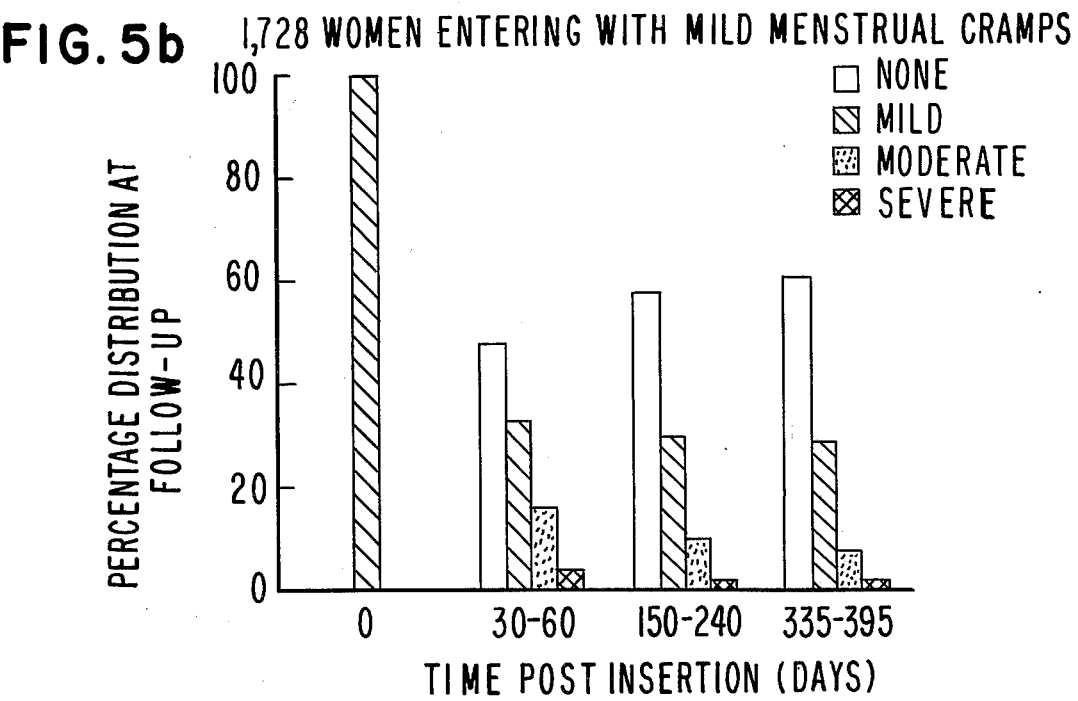
FIG. 5b 1,728 WOMEN ENTERING WITH MILD MENSTRUAL CRAMPS

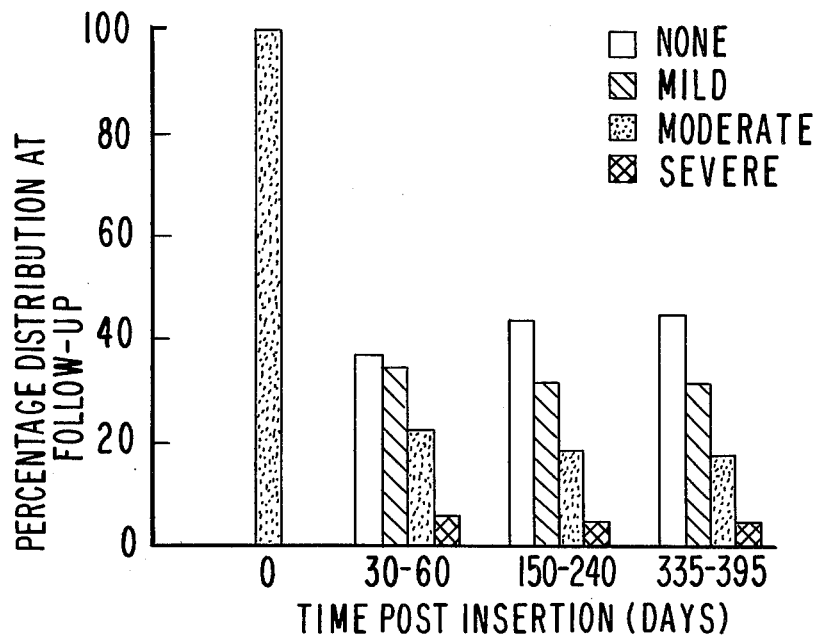
FIG. 5c 744 WOMEN ENTERING WITH MODERATE MENSTRUAL CRAMPS
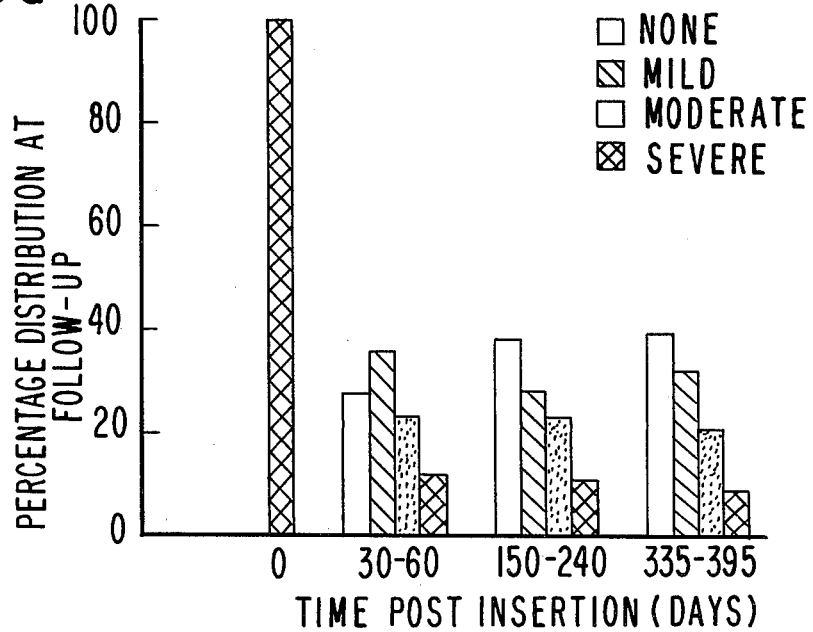
FIG. 5d 253 WOMEN ENTERING WITH SEVERE MENSTRUAL CRAMPS

METHOD FOR TREATING DYSMENORRHEA WITH A UTERINE THERAPEUTIC SYSTEM

BACKGROUND OF THE INVENTION

1. Field of the Invention

This invention pertains to gynecologic pharmacology. More particularly, the invention relates to a method for the management of dysmenorrhea by administering a progestational hormone in an effective amount to the uterus of an animal afflicted with dysmenorrhea.

2. DESCRIPTION OF THE PRIOR ART

Dysmenorrhea is clinically the presence of uterine cramps occurring prior to, coincident with the onset, or during menstruation. It is one of the most common gynecological complaints and it represents a major cause of lost school and working days. Premenstrual cramps alone are responsible in industry for up to 43 percent of absentee days per month per 100 women. At present, no effective treatment has been devised by the prior art for women suffering with dysmenorrhea other than mild analgesia, or simply to make the best of their situation as "part of the woman's lot". The prior art has administered low doses of progesterone over a prolonged period of time locally to the uterus for fertility control, Scommegna, A., et al, *Obst. and Gynec.*, Vol. 43, No. 5, pages 769 to 779, 1974, and it has administered progestin from intrauterine devices to minimize contractility thereby lessening the expulsion rate of intrauterine devices, Doyle, et al, *Am. J. Obst. & Gynec.*, Vol. 101, No. 4, pages 564 to 568, 1968 and British Pat. No. 1,318,554, but it has not administered progestational steroids to the uterus for the management of dysmenorrhea. In view of the above presentation, it becomes immediately apparent that a critical need exists for a method useful for the management of dysmenorrhea, and if such a method were made available, it would represent a valuable contribution to the useful medical arts.

OBJECTS OF THE INVENTION

Accordingly, it becomes an immediate object of this invention to provide a method useful for the management of dysmenorrhea to give relief to a person afflicted with dysmenorrhea.

Still another object of the invention is to provide a method for treating a female suffering with dysmenorrhea comprising locally releasing in the female's uterine cavity a therapeutically effective amount of at least one progestational steroid to relieve cramps and other infirmities associated with dysmenorrhea.

Yet another object of the invention is to provide a method for treating dysmenorrhea consisting essentially of administering a progestational steroid to the uterine endometrium in controlled and continuous low concentrations over an extended duration of time for substantially reducing the discomfort of dysmenorrhea.

Other objects, features and unobvious advantages of the invention will be more apparent to those skilled in the art from a reading of the present disclosure and the accompanying claims.

SUMMARY OF THE INVENTION

This invention concerns a method for the management of dysmenorrhea comprising administering a progestational steroid to the uterus in an amount needed to produce relief from dysmenorrhea. The method uses small doses of progestational steroids and achieves the effect without administering excessive amounts to the uterus and it is substantially free of systemic absorption.

Specifically, the method comprises administering a progestational steroid to the uterus from an intrauterine therapeutic system in a controlled and continuous therapeutically effective low dosage amount up to 100 micrograms per hour over a prolonged period of up to 3 years to relieve cramps and discomfort of dysmenorrhea.

BRIEF DESCRIPTION OF THE DRAWINGS

In the drawings, which are not drawn to scale, but are set forth to illustrate various embodiments of the invention, the figures are as follows.

In the drawings and specification, like parts in related Figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 1:
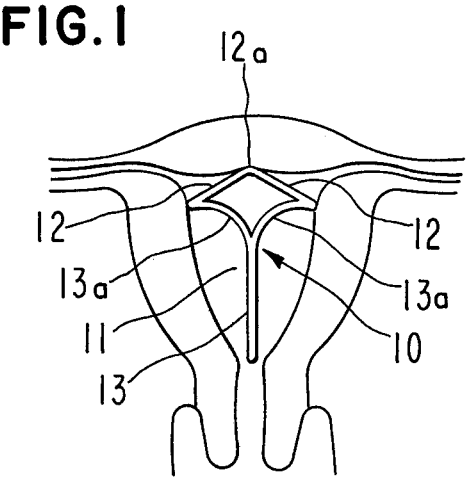
FIG. 1 is a sectional view of the uterine cavity showing an intrauterine device properly positioned in the cavity.

Turning now to the drawings in detail, which are examples of intrauterine therapeutic systems that can be used for releasing a progestational hormone to the uterus for the management of dysmenorrhea and which examples are not to be construed as limiting the invention, one embodiment thereof is seen in FIG. 1. The phrase "intrauterine therapeutic system" as used herein embraces "intrauterine therapeutic system in the form of an intrauterine therapeutic device", "intrauterine device", and "system", and for the purpose of the invention, these are deemed as functional equivalents. In FIG. 1, an intrauterine device 10 is seen in uterus 11 positioned for releasing progestational hormone to uterus 11. Device 10 is comprised of a transverse arm 12 having a flexure 12a with arm 12 suitably united to a dependent arcuate arm 13 bent concavely 13a and extended downward from arm 12 to define a device having a shape that is sized and adapted for prolonged placement in uterus 11. Device 10 is made of biologically inert materials and for this invention it is manufactured with releasing means comprising saturating the device with progestational steroid or manufacturing the device with an internal reservoir containing progestational steroid, both not shown in FIG. 1.

Figure 2:
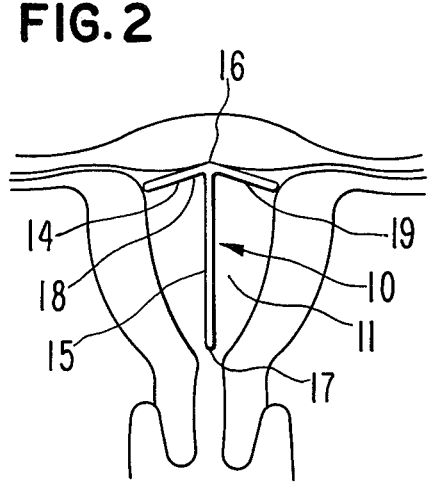
FIG. 2 is a view illustrating an intrauterine device having a transverse member and a perpendicular member placed in the uterus.

In FIG. 2 an intrauterine device 10 is seen comprised of a transverse member 14 suitably fixed to a dependent member 15. Member 15 has a front end 16 and a distant end 17. Member 14 interconnects with dependent member 15 at front end 16 with member 14 extended outwards in two directions from member 15 to define arm 18 and arm 19, a right and left arm respectively. Arms 18 and 19 each terminate in a rounded end to prevent any possible damage to uterine cavity 11. Device 10 is substantially T-shaped and it is sized and shaped to fit all uterine cavities. Its dimensions can be made to conform to the nulliparous and multiparous uterine cavities. Generally, members 14 and 15 have a length of 20 to 40 millimeters and a diameter of 1 to 4 millimeeters. Device 10 for the purpose of this invention is manufactured with steroid releasing means, not shown in FIG. 2. The releasing means can comprise steroid distributed throughout the device when formed of a solid polymeric filament, or the steroid can be housed in a reservoir. An intrauterine T-shaped device as described above was disclosed by Tatum, H. J., in U.S. Pat. No. 3,533,406. Another intrauterine device similar to the device described above and suitable for the present purpose is the 7-shaped device as disclosed by Abramson, H. J., in U.S. Pat. No. 3,777,748.

Figure 3:
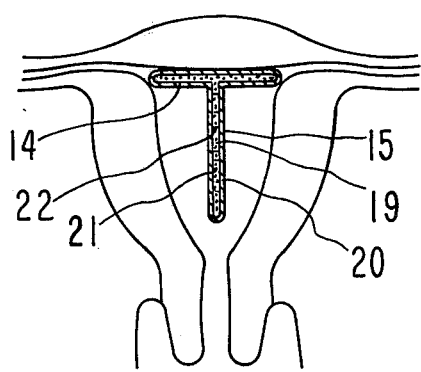
FIG. 3 is a cross-sectional view of the intrauterine device of FIG. 2 manufactured with a drug reservoir.

FIG. 3 illustrates device 10 of FIG. 2 in cross-section manufactured with a reservoir 19 for containing a progestational agent 21. Reservoir 19 is formed by a wall 20 surrounding an internal space in members 14 or 15 containing agent 21 and a carrier 22 permeable to the passage of agent 21. Wall 20 is formed of a release rate controlling material permeable to the passage of agent 21 but at a lower rate than through carrier 22. In operation, agent 21 dissolved in carrier 22 is released from device 10 by diffusion through wall 20 at a rate controlled by wall 20. The device of FIG. 3 is described in U.S. Pat. No. 3,845,761 which patent is assigned to the Alza Corporation of Palo Alto, Calif. and incorporated by reference herein.

Figure 4:
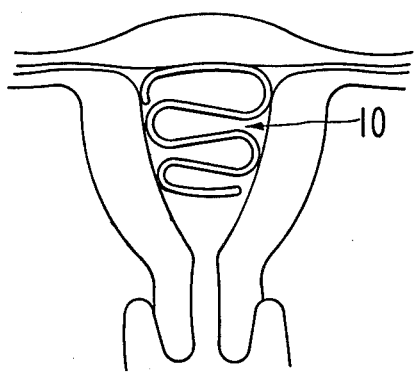
FIG. 4 is a view depicting an intrauterine device having a continuous curved shape positioned in the uterus; and, FIGS. 5a, 5b, 5c, and 5d represent the results obtained by practicing the method of the invention.

FIG. 4 illustrates another device 10 that can be adapted to release progestational steroids for the method of the invention. In this figure, device 10 is comprised of an elongated body 19 arranged in sinous form. Device 10 is substantially in one plane with imaginary boundaries of an isoseceles trapezoid. The device of FIG. 4 shaped like a large S continuing into a smaller S was disclosed by Lippes, J., in U.S. Pat. No. 3,250,271.

DETAILED DESCRIPTION OF THE INVENTION

This invention resides in the unexpected discovery that progestational steroids can be administered in low dosage amounts to the uterus for the relief of dysmenorrhea. The method comprises administering progestational steroids and their physiologically active derivatives from an intrauterine delivery device positioned in the uterus to the uterus and its surrounding tissues in controlled and continuous therapeutically effective amounts over a prolonged period of time. The progestational steroid is administered from the device according to a precise dosage program. The purpose of the dosage program is to administer the progestational steroid in an amount required for alleviating dysmenorrhea while simultaneously avoiding substantially introducing the steroid into systemic circulation and saturating the uterine tissues with unneeded progestational agent. The amount of progestational steroid administered is an effective amount for relief of dysmenorrhea up to 100 micrograms per hour over a prolonged period of up to 3 years, or longer. In a presently preferred embodiment, the amount administered is from 5 nanograms up to 100 micrograms per day over a prolonged period of 1 to 2 years. Generally, the intrauterine device contains an amount sufficient to provide relief from dysmenorrhea over a prolonged period of time, usually about 0.1 mg to 5 grams or more of at least one or a mixture of progestational steroids.

In the specification and the accompanying claims the phrase "progestational agent" broadly includes substances possessing a cyclopentanophenanthrene nucleus of naturally occurring or synthetic origin. The term "agent" broadly includes hormones and steroids and these terms are considered interchangeable. The term "progestational" as used herein also embraces progestogens and progestins. Progestational agents useful for the purpose of the present invention are represented by the following formula:

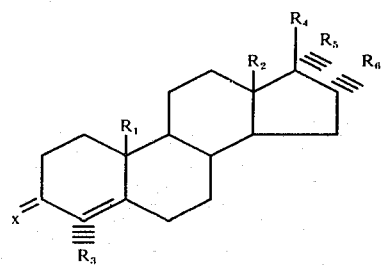

wherein $R_1$, $R_2$ and $R_3$ are independently selected from the group consisting of hydrogen and lower alkyl, $R_4$ is a member selected from the group consisting of hydroxyl and acyl, $R_5$ and $R_6$ are independently selected from the group consisting of hydrogen, hydroxyl, and acyloxy, $R_5$ and $R_6$ taken together is a

group wherein $w$ is a lower alkyl and $p$ is a member selected from the group consisting of lower alkyl and phenyl, and $x$ is oxygen or $H_2$; and a steroid of the formula:

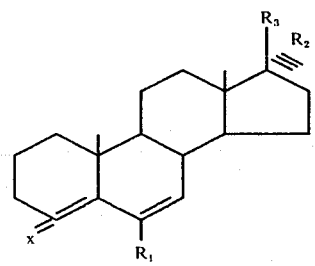

wherein $x$ is a member selected from the group consisting of oxygen and $H_2$, $R_1$ is a member selected from the group consisting of lower alkyl and chlorine, $R_2$ is a member selected from the group consisting of lower alkyl and acyloxy, and $R_3$ is an acyl group; a steroid of the general formula:

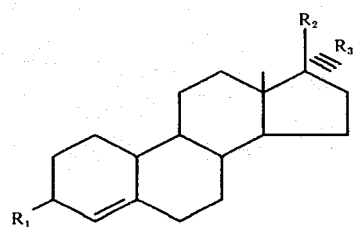

wherein R₁ is a member selected from the group consisting of hydroxyl and acyloxy, R₂ is a member selected from the group consisting of hydrogen and acyloxy, and R₃ is an alkynyl; and a steroid of the general formula:

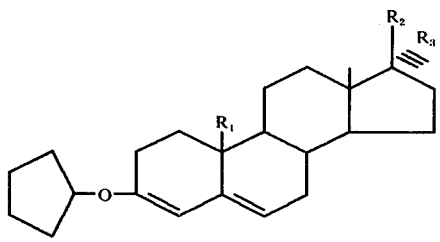

wherein R₁ is a member selected from the group consisting of hydrogen and lower alkyl, R₂ is a member selected from the group consisting of acyl and acyloxy, and R₃ is a member selected from the group consisting of hydroxyl and alkynyl.

In the above, the term "lower alkyl" embraces straight and branched chain alkyl groups of 1 to 7 carbon atoms inclusive, the term "alkynyl" embraces straight and branched chain alkynyl groups of 2 to 7 carbon atoms inclusive, the term "acyl" embraces acyl groups of 1 to 20 carbon atoms including alkanoyl of 1 to 20 carbons and alkenyl of 2 to 20 carbons, and the term "acyloxy" embraces acyloxy groups of 1 to 20 carbons including alkanoxyloxy of 1 to 20 and alkenyloxy groups of 2 to 20 carbons inclusive.

Exemplary steroids possessing progestational activity embraced by the above formula include progesterone or Δ⁴-pregnene-3,20-dione; medroxyprogesterone or 6α-methyl-4-pregnen-17α-ol-3,20-dione; 6α-methyl-17α-acetoxyprogesterone; ethisterone or 17α-ethynyl-17β-hydroxy-4-androsten-3-one; dimethisterone or 6α-methyl-17-(1-propynyl)-testosterone; norethindrone or 17-hydroxy-19-nor-17α-pregn-4-en-20-yn-3-one; norgestrel or (+)-13-ethyl-17α-ethynyl-17-hydroxygon-4-en-3-one; norethynodrel or 17-hydroxy-19-nor-17α-pregn-5(10)-en-20-yn-3-one; ethynodiol diacetate or 3β,17β-diacetoxy-17α-ethynyl-4-estrene; ethynodiol or 19-nor-17α-pregn-4-en-20-yne-3β,17-diol; quingestanol acetate or 3-(cyclopentoxyl)-19-nor-17α-pregna-3,5-dien-20-yn-17-ol-acetate; lynestrenol or 17α-ethynylester-4-en-17β-ol; 17α-acetoxyprogesterone or 17α-acetoxypregn-4-ene-3,20-dione; 17α-hydroxyprogesterone; 17α-hydroxypregesterone 3-cyclopentyl enol ether; megestrol acetate or 17α-hydroxy-6-methylpregna-4,6-diene-30,20-dione acetate; chlormadinone acetate or 6-chloro-17-hydroxypregna-4,6-diene-3,20-dione acetate; megrogestone or 6,17-dimethylpregna4,6-diene-3,20-dione; dydrogesterone or 10α-pregna-4,6-diene-3,20-dione; acetophenonide or R-16α,17-dihydroxy-pregn-4-ene-3,20-dione; quingestrone or 3-(cyclopentyloxy)pregna-3,5-dien-20-one; alphasone or 16α,17-dihydroxypregn-4-ene-3,20-dione; algestone acetophenide or 16α,17α-dihydroxy-4-pregnene-3,20-dione, cyclic 16,17-acetal with acetophenone (β-methyl-α-phenyl); 17α-ethynyl-5-estren-17β-ol; and norgestrienone or 17α-ethynyl-17-hydroxy-estra-4,6,11-trien-3-one. The steroids are known to the art in U.S. Pat. Nos. 2,744,122; 2,725,389; 3,176,013; 3,000,883; 2,753,360; 3,179,675; 2,379,882; 3,000,914; 3,147,290 and 2,927,119; and in Bev., Vol. 71, p. 1024, 1938; Chem. & Ind., p. 905, 1959; J. Am. Chem. Soc., Vol. 82, p. 746, 1960; Tetrahedron, Vol. 19, p. 289, 1963; British Pat. No. 870,286; and, German Pat. No. 1,075,114.

The above progestational steroids can be used as the pharmacologically acceptable derivatives thereof, such as the derivative of their hydroxy or keto groups. Such derivatives should convert to the parent compounds upon release from the intrauterine system by enzymatic transformation, pH assisted hydrolysis, and the like. Suitable derivatives include hydrolyzable esters with pharmaceutically acceptable acids, such as formate, acetate, propionate, butyrate, valerate, caproate, hexanate, heptanoate, caprylate, maleate, citrate, perlargonate, succinate, tartrate, fumarate, malate, ascorbate, sulphate, phosphate, and the like. Of course, the acyl radical of other organic carboxylic acids containing 1 to 20 carbons can be used. These include the residue of hydrocarbon carboxylic acids, such as alkanoyl and alkenoyl. These residues are known to the Description of the Prior Art 2,873,271; 3,415,818 and 3,892,842. The last cited patent is assigned to the Alza Corporation, Palo Alto, Calif.

Carriers suitable for the present purpose include propylene glycol, silicone oil, glycerin, corn oil, saline and the like. Materials suitable for the wall of a reservoir device include vinylchloride diethylfumarate, poly(dimethylsiloxane), cross-linked partially hydrolyzed insoluble poly(vinyl alcohol), ethylene/vinyl acetate copolymer, and the like. Exemplary of other carriers, manufacturing procedures and wall forming materials are described in U.S. Pat. Nos. 3,845,761 and 3,896,819 which patents are herein incorporated by reference. These patents are assigned to the Alza Corporation, Palo Alto, Calif.

The method of the invention is performed in a presently preferred embodiment by positioning a T-shaped intrauterine device containing progesterone in the uterus of a woman suffering with dysmenorrhea for releasing progesterone thereto. The device used administered about 50 to 70 micrograms per day to the uterus over a prolonged period of 1 year. The device is made of ethylene-vinyl acetate copolymer and its reservoir contains progesterone in silicone oil. The device is disclosed in U.S. Pat. No. 3,845,761, which patent is herein incorporated by reference.

At the time of placement and at follow-up visits, the women were asked to rate their dysmenorrhea cramps as none, mild, moderate or severe. The follow-up visits occurred between 30–60, 150–240 and 335–395 days after placement of the uterine therapeutic system. The results of controlled and continuous administration of progesterone to the uterus over a prolonged period of time indicated a substantial improvement in the management of dysmenorrhea. The results are recorded in accompanying FIGS. 5a, 5b, 5c, and 5d. FIG. 5a represents the results obtained when the system was placed in the uterus of 3,531 women reporting no menstrual cramps at the time the system was inserted in the uterus. FIG. 5b represents the results obtained when the system was placed in the uterus of 1,728 women who had a recent history of mild menstrual cramps at the time of placement. FIG. 5c represents the results for 744 women who reported a recent history of moderate menstrual cramps at the time of placement, and FIG. 5d represents the results for 253 women who reported a recent history of severe dysmenorrhea as indicated by menstrual cramps at the time the progestational releasing system was placed in the uterus.

It will be understood by those versed in the art in the light of the present specification, drawings and accompanying claims that this invention makes available both a novel and useful method for the management of dysmenorrhea that represents an unexpected valuable contribution to the medical art. And, it will be further understood by those versed in the art that many different embodiments of this invention can be made without departing from the scope of the invention. Accordingly, it is to be understood the invention is not to be construed as limited, but it embraces all equivalents inherent therein.

What is claimed is:

1. A method for treating dysmenorrhea in a warm blooded animal which method comprises administering to the uterus of the animal from a means sized, shaped and adapted for placement in the uterus a therapeutically effective amount of a progestational steroid for a prolonged period of time to impart relief from said dysmenorrhea.

2. The method for treating dysmenorrhea according to claim 1 wherein the means is made of a progestational steroid release rate controlling material that releases a therapeutically effective amount up to 100 micrograms per hour over a prolonged period of up to 3 years.

3. The method for treating dysmenorrhea according to claim 1 wherein the progestational steroid is progesterone.

4. The method for treating dysmenorrhea according to claim 1 wherein the progestational steroid is administered from a means in the form of an intrauterine device sized, shaped and adapted for insertion and retention in the uterus with the device comprising a reservoir housing the progestational steroid and having a release rate controlling wall for releasing the progestational steroid in controlled amounts from the device.

5. The method for treating dysmenorrhea according to claim 4 wherein the device comprises a transverse member and a dependent member connected to the transverse member.

6. The method for treating dysmenorrhea according to claim 4 wherein the device is T-shaped and the release rate controlling wall is formed of an ethylene-vinyl acetate copolymer.

7. The method for the management of dysmenorrhea according to claim 1 wherein the progestational steroid is progesterone and the therapeutically effective amount is 50 to 70 micrograms per day.

8. A method for the management of dysmenorrhea which comprises administering to the uterus of a warm blooded animal having dysmenorrhea a therapeutically effective amount of a progestational hormone having the following formula:

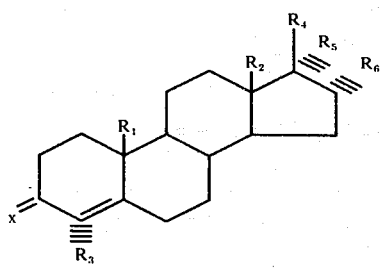

wherein $R_1$, $R_2$ and $R_3$ are independently selected from the group consisting of hydrogen and lower alkyl; $R_4$ is a member selected from the group consisting of hydroxyl and acyl; $R_5$ and $R_6$ are independently selected from the group consisting of hydrogen, hydroxyl and acyloxy; $R_5$ and $R_6$ taken together consists of a

group wherein $w$ is a lower alkyl and $p$ is a member selected from the group consisting of lower alkyl and phenyl and $x$ is a member selected from the group consisting of $H_2$ and oxygen.

9. A method for the management of dysmenorrhea which comprises administering to the uterus of a warm blooded animal having dysmenorrhea an effective amount of a progestational hormone having the following formula:

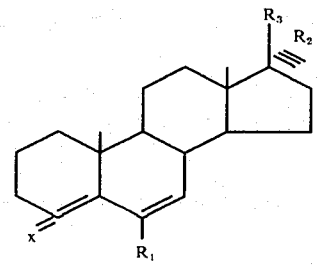

wherein $x$ is a member selected from the group consisting of oxygen and $H_2$; $R_1$ is a member selected from the group consisting of lower alkyl and halogen; $R_2$ is a member selected from the group consisting of lower alkyl and acyloxy; and $R_3$ is an acyl moiety.

10. A method for the management of dysmenorrhea which comprises administering to the uterus of a warm blooded animal having dysmenorrhea a progestational hormone having the following formula:

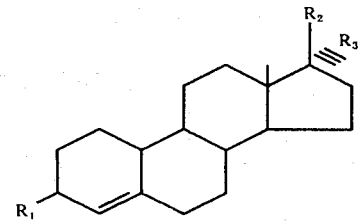

wherein $R_1$ is a member selected from the group consisting of hydroxyl and acyloxy; $R_2$ is a member selected from the group consisting of hydrogen and acyloxy; and $R_3$ is alkynyl.

11. A method for the management of dysmenorrhea which comprises administering to the uterus of a warm blooded animal having dysmenorrhea a progestational hormone having the following formula:

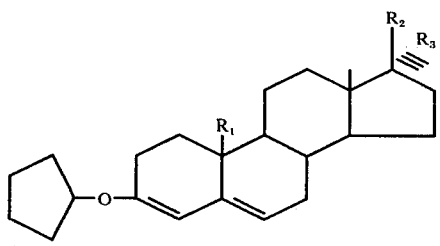

wherein $R_1$ is a member selected from the group consisting of hydrogen and lower alkyl; $R_2$ is a member selected from the group consisting of acyl and acyloxy; and $R_3$ is a member selected from the group consisting of hydroxyl and lower alkynyl.

12. A method for treating dysmenorrhea which comprises administering to the uterus of a woman having dysmenorrhea a therapeutically effective amount of a progestational steroid from a uterine therapeutic system in the form of an intrauterine device that releases the steroid selected from the group consisting of $\Delta^4$-pregnene-3,20-dione; 6α-methyl-4-pregnen-17α-ol-3,2-dione; 6α-methyl-17α-acetoxyprogesterone; 17α-ethynyl-17β-hydroxy-4-androsten-3-one; 6α-methyl-17-(1-propynyl)testosterone; 17-hydroxy-19-nor-17α-pregn-4-en-20-yn-3-one; (±)-13-ethyl-17α-ethynyl-17-hydroxygon-4-en-3-one; 17-hydroxy-19-nor-17α-pregn-5(10)-en-20-yn-3-one; 3β,17β-diacetoxy-17α-ethynyl-4-estrene; 19-nor-17α-pregn-4-en-20-yne-3β,17-diol; 3-(cyclopentoxyl)-19-nor-17α-pregna-3,5-dien-20-yn-17-ol-acetate; 17α-ethynylester-4-en-17β-ol; 17α-acetoxypregn-4-ene-3,20-dione; 17α-hydroxyprogesterone; 17α-hydroxyprogesterone 3-cyclopentyl enol ether; 17α-hydroxy-6-methylpregna-4,6-diene-3,20-dione acetate; 6-chloro-17-hydroxypregna-4,6-diene-3,20-dione acetate; 6,17-dimethylpregna-4,6-diene-3,20-dione; 10α-pregna-4,6-diene3,20-dione; R-16α,17-dihydroxy-pregn-4-ene-3,20-dione; 3-(cyclopentyloxy)pregna-3,5-dien-20-one; 16α,17-dihydroxypregn-4-ene-3,20-dione; 16α,17α-dihydroxy-4-pregnene-3,20-dione, cyclic 16,17-acetal with acetophenone; 17α-ethynyl-5-estren-17β-ol; and 17α-ethynyl-17-hydroxy-estra-4,6,11-trien-3-one, in a controlled and continuous amount over a prolonged period of time.

13. The method for treating dysmenorrhea according to claim 12 wherein the progestational steroid is administered as a pharmaceutically acceptable ester of a member selected from the group consisting of alkanoyl of 1 to 20 carbons and alkenyl of 2 to 20 carbons.

14. The method for treating dysmenorrhea according to claim 12 wherein the uterine therapeutic system is made of ethylene-vinyl acetate copolymer.

15. The method for treating dysmenorrhea according to claim 12 wherein the uterine system is sized, shaped and adapted for prolonged placement in the uterus and is formed of a biologically inert polymer having progestational steroid dispersed therein that is released from the system to the uterus in a therapeutically effective amount of 5 nanograms to 100 micrograms per day to impart relief from said dysmenorrhea.

16. A method for treating dysmenorrhea according to claim 12 wherein the uterine system is sized, shaped and adapted for prolonged placement in the uterus and is formed with an internal reservoir containing the progestational steroid.

17. The method for treating dysmenorrhea according to claim 12 wherein the uterine therapeutic system is 7-shaped or is in the shape of a large S continuing into a smaller S.

18. A method for treating dysmenorrhea which method comprises the steps of (a) positioning in the uterus of a woman having dysmenorrhea an intrauterine device sized, shaped and adapted for prolonged retention in the uterus and containing 0.1 milligrams to 5 grams of a progestational steroid and (b) administering from the device from 5 nanograms to 100 micrograms per day of the progestational steroid to the uterus to impart relief from said dysmenorrhea.

19. The method for treating dysmenorrhea according to claim 18 wherein the progestational steroid is progesterone and it is administered to the uterus substantially free of systemic absorption.

* * * * *